United States Patent [19]

Bienayme

[11] Patent Number: 5,563,297

[45] Date of Patent: Oct. 8, 1996

[54] INTERMEDIATES FOR THE PREPARATION OF VITAMIN A AND CAROTENOIDS AND PROCESS FOR THEIR PREPARATION

[75] Inventor: Hugues Bienayme, Lyons, France

[73] Assignee: Rhone-Poulenc Nutrition Animale, Antony, France

[21] Appl. No.: 320,150

[22] Filed: Oct. 7, 1994

[30] Foreign Application Priority Data

Oct. 7, 1993 [FR] France .................................. 93 11943

[51] Int. Cl.$^6$ .................................................. C07C 45/67
[52] U.S. Cl. ........................ 568/314; 568/335; 568/320; 568/467
[58] Field of Search .................................. 568/314, 335, 568/320, 467

[56] References Cited

U.S. PATENT DOCUMENTS

| | | | |
|---|---|---|---|
| 3,057,888 | 10/1962 | Marbet et al. | 568/313 |
| 3,225,102 | 12/1965 | Thompson | 260/598 |
| 3,236,869 | 2/1966 | Thompson | 568/467 |
| 4,362,670 | 12/1982 | Woo | 568/314 |

FOREIGN PATENT DOCUMENTS

| | | | |
|---|---|---|---|
| 1313362 | 11/1962 | France | 568/319 |

OTHER PUBLICATIONS

"Chemical Abstracts", vol. 103, No. 15, Oct. 14, 1985, Columbus Ohio, US: abstract No. 123059d, 'Alpha-Beta-Unsaturated Carbonyl Compounds'.

Primary Examiner—James H. Reamer
Attorney, Agent, or Firm—Finnegan, Henderson, Farabow, Garrett & Dunner, L.L.P.

[57] ABSTRACT

The present invention relates to novel intermediates for the preparation of vitamin A and carotenoids, corresponding to the following formula (I):

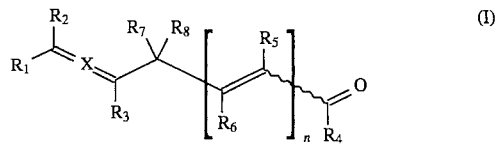

in which X is a carbon atom; n is equal to 1 or 2; $R_1$, $R_2$ and $R_3$, which may be identical or different, each independently represent hydrogen, alkyl containing 1 to 4 carbon atoms, alkenyl containing 2 to 11 carbon atoms or aryl, each alkyl and alkenyl may be linear, branched or cyclic, or $R_1$ and $R_2$ can together with the carbon atom to which they are attached form a cycloaliphatic compound which is optionally substituted; and $R_4$, $R_5$, $R_6$, $R_7$ and $R_8$, which may be identical or different, each independently represent hydrogen, alkyl containing 1 to 4 carbon atoms or alkenyl containing 2 to 10 carbon atoms, each alkyl or alkenyl being linear, or if containing sufficient numbers of carbon atoms, may also be branched or cyclic, or an aryl containing 6 to 10 carbon atoms, or any two of $R_4$, $R_5$, $R_6$, $R_7$ and $R_8$ may together form, along with the carbon atom(s) to which they are attached, a cycloalkylidene group containing 3 to 10 carbon atoms, as well as the process for their preparation and their use.

2 Claims, No Drawings

INTERMEDIATES FOR THE PREPARATION OF VITAMIN A AND CAROTENOIDS AND PROCESS FOR THEIR PREPARATION

The present invention relates to novel intermediates for the preparation of vitamin A and carotenoids.

The disclosure of U.S. patent application Ser. No. 08/320,185, filed Oct. 7, 1994, entitled "Intermediates for the Preparation of Vitamin A and Carotenoids and Process for this Preparation," and naming Hugues Bienayme and Pierre Meilland as inventors, is specifically incorporated by reference herein.

The present invention relates more particularly to intermediates corresponding to the following formula (I):

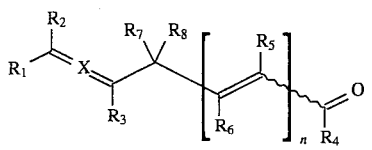

in which

X is a carbon atom, n is equal to 1 or 2, $R_1$, $R_2$ and $R_3$, which may be identical or different, each independently represent hydrogen, alkyl containing 1 to 4 carbon atoms, alkenyl containing 2 to 11 carbon atoms or aryl, wherein each alkyl and alkenyl may be linear, branched or cyclic, or $R_1$ and $R_2$ can together with the carbon atom to which they are attached form a cycloalkyl compound which is optionally substituted, $R_4$, $R_5$, $R_6$, $R_7$ and $R_8$, which may be identical or different, each independently represent hydrogen, alkyl containing 1 to 4 carbon atoms or alkenyl containing 2 to 10 carbon atoms, each alkyl or alkenyl being linear, branched or cyclic, or an aryl containing 6 to 10 carbon atoms, or any two of $R_4$, $R_5$, $R_6$, $R_7$ and $R_8$ may together form, along with the carbon atom(s) to which they are attached, a cycloalkylidene group containing 3 to 10 carbon atoms. Preferably, when two of $R_4$, $R_5$, $R_6$, $R_7$ and $R_8$ together form an alkylidene containing 2 to 10 carbon atoms, both groups are attached to adjacent carbon atoms. As is understood by one skilled in the art, an alkenyl group or an alkyl group can be branched or cyclic only if it contains more than two carbon atoms.

Among the compounds of formula (I), those are preferred in which $R_4$, $R_5$, $R_7$ and $R_8$ represent hydrogen and $R_6$ represents methyl.

Among the compounds of formula (I), those are very particularly preferred in which $R_1$ represents the following group (unit):

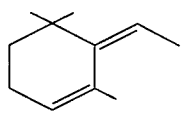

$R_2$ represents methyl and $R_3$ represents hydrogen.

Compounds of formula (I) are prepared by rearranging, in the presence of a catalyst based on a transition metal, a compound of the following formula (II):

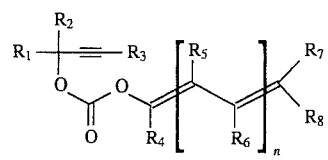

in which $R_1$, $R_2$, $R_3$, $R_4$, $R_5$, $R_6$, $R_7$ and $R_8$ and n have the same meaning as in formula (I).

As is evident in formula (II), there is a triple bond between two carbon atoms; $R_3$ is bonded to one of the carbon atoms, and the carbon atom to which $R_1$ and $R_2$ are bonded is itself bonded second of the two carbon atoms.

As defined herein, all alkyl, alkenyl, cycloalkyl, cycloalkenyl, cycloalkylidene and aryl groups can be substituted or unsubstituted unless otherwise stated.

The compounds of the following formula (II) are very particularly preferred:

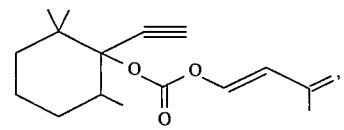

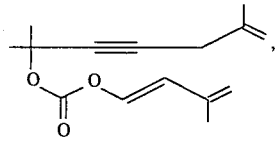

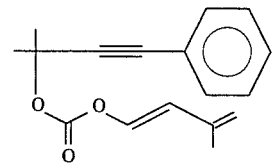

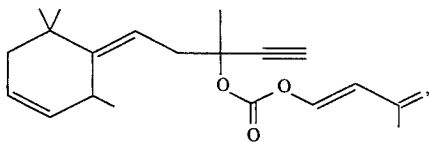

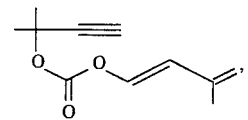

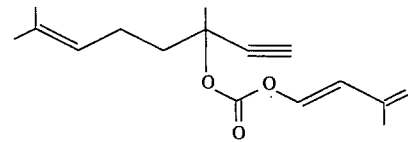

The transition metal is in particular chosen from the of columns VIII, $I_B$ and $II_B$ of the Periodic Classification (i.e., the Periodic Table). It is preferred to use nickel or palladium.

The transition metal may be used in the presence of a ligand chosen from phosphorus compounds such as bis-diphenylphosphinoethane, triphenylphosphine, trimethoxyphenylphosphine, triisopropyl phosphite, trifluorophenylphosphine, trithiophenylphosphine, tritolylphosphine and trinaphthylphosphine. The reaction preferably takes place in an aprotic solvent.

The amount of catalyst introduced advantageously ranges from 1 to 20%, calculated as atom equivalents of metal relative to the compound of formula (II).

The compounds of formula (I) are advantageously converted into terpene aldehyde or vitamin A intermediates by the action of a base chosen from alkali metal and alkaline-earth metal carbonates or alkoxides or by the action of an acid such as hydrobromic acid.

The present invention will be more completely described with the aid of the following examples, which should not be considered as limiting the invention.

EXAMPLE 1

Preparation of ethynyl-retro-α-ionol 2-methyl-1,3-butadien-4-ol carbonate

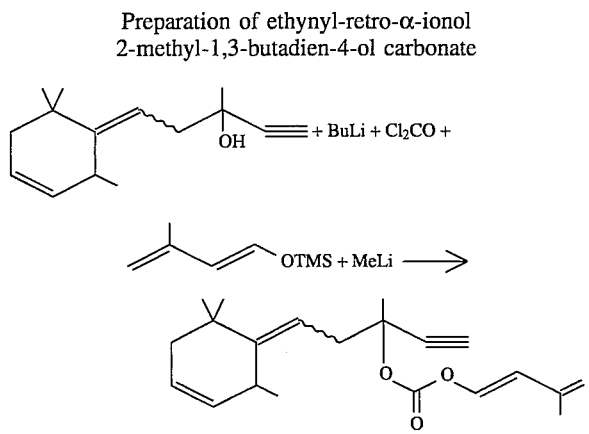

I) 2.86 ml of butyllithium in hexane ($4.58 \times 10^{-3}$ mol) was added, under argon, to 10 ml of anhydrous THF containing 1 g of ethynyl-retro-α-ionol ($4.58 \times 10^{-3}$ mol) maintained at −20° C. Following this addition, the mixture was left to stand for approximately 10 minutes and was then added to a solution of phosgene in toluene (2.36 ml, 4.57 mmol) at −40° C.

Following this addition, the solution turned a yellow-orange color.

II) 3.75 ml of methyllithium ($6 \times 10^{-3}$ mol) dissolved in ether was added, at −40° C., to 10 ml of THF containing $6.46 \times 10^{-3}$ mol of prenal silyl enol ether. The mixture was left to stand for 15 minutes and was then added, at −40° C., to the chloroformate prepared in I.

The mixture was left to stand for 30 minutes at −40° C. and was then diluted with ethyl ether and washed with saturated aqueous sodium chloride solution. The mixture was then re-extracted with ether.

After chromatography, 1.176 g of product was obtained (yield 78%), the NMR, infrared and mass analyses of which confirmed the expected structure.

EXAMPLES 2 TO 8

In accordance with the procedures employed in Example 1, the carbonates, whose preparation yields are indicated in Table 1, were prepared according to the following reaction:

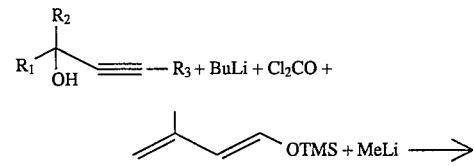

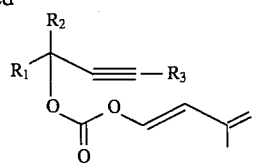

EXAMPLE 9

(Table 1)

I) Preparation of prenyl chloroformate

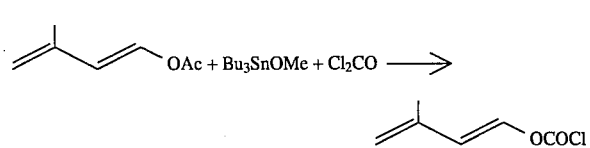

Methoxytributyltin (7 ml, 24.3 mmol) under argon was added to freshly distilled acetoxyisoprene (3.26 g, 25.8 mmol) at 0° C. Stirring was carried out at room temperature for 30 minutes, followed by dilution with 20 ml of methylene chloride and by addition, at 0° C., to a toluene solution of phosgene (12.5 ml, 24 mmol).

The mixture was left stirring at 0° C. for 15 minutes, and the methylene chloride was then evaporated off. The toluene and the product were subsequently distilled off at reduced pressure (100° C., 90–100 mm of mercury).

1.32 g of a pale yellow liquid containing 74% by weight of expected chloroformate (NMR) was recovered. The yield was 28%.

II) Preparation of the carbonate

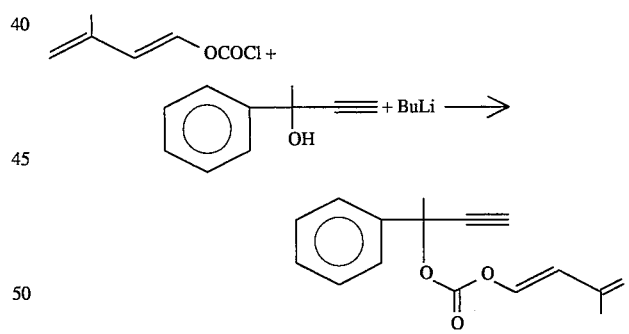

2-Phenyl-3-butyn-2-ol (0.664 g, 4.54 mmol) was dissolved in 5 ml of anhydrous tetrahydrofuran under argon. The mixture was cooled to −40° C. and butyllithium (1.6 molar solution in hexane, 3 ml, 4.8 mmol) was added. The mixture was left stirring at −40° C. for 10 minutes, followed by addition of the chloroformate prepared in I (1.20 g, 6 mmol) in 1.5 ml of tetrahydrofuran. After 30 minutes at −40° C., the mixture was diluted with a solution of triethylamine in ethyl ether, washed with water at −20° C., dried over magnesium sulphate, evaporated under reduced pressure and then chromatographed, and the expected product (0.911 g) was recovered. The yield was 78%.

EXAMPLES 1 TO 13—REARRANGEMENT
(Tables 1 and 2)

The carbonate of Example 2, $R_1=R_2=CH_3$ and $R_3=H$, (0.343 g, 1.77 mmmol), was dissolved in 6 ml of anhydrous tetrahydrofuran under argon. The catalyst (0.100 g, 0.086 mmol, 5%) was added at room temperature and the mixture was then brought to 65° C.

The reaction was monitored by thin layer chromatography (eluent: pentane/ether 10/1). The carbonate had disappeared after 1 hour 30 minutes. The solvent was evaporated off and the mixture was then chromatographed on silica (eluent: pentane/ether 10/1).

Two fractions were separated:
fraction a: mass 0.0568 g; product Ia, wherein X is a carbon atom; yield=21%
fraction b: mass 0.1019 g; product Ib; yield=38%.

Examples 1 to 9 were performed according to the same experimental procedure as Example 2, and the results are indicated in Table 1. Examples 10 to 13 were performed according to the same experimental procedure as Examples 1 to 9 with various catalysts and various ligands, and the results are indicated in Table 2. In all of Examples 2 to 13, X in product Ia is a carbon atom.

EXAMPLES 14 TO 18

Preparation of various carbonates according to the same experimental procedure as that of Example 1.

The carbonate was rearranged in the presence of catalysis with 5% $Pd(PPh_3)_4$ in THF (Conc.=0.2) at 55°–60° C.

The compounds obtained and their respective yields are indicated in Table 3.

EXAMPLE 19

Example 16 was reproduced using-as rearrangement catalyst 20% $Ni(COD)_2$ and 40% $PPh_3$ in THF at room temperature for 3 hours. The following compound was obtained with a yield of 62%:

wherein X is a carbon atom.

EXAMPLE 20

Use of a compound of formula (I) to prepare an isomer of retinal 0.069 g ($0.244\times10^{-3}$ mol) of the intermediate obtained in Example 1 (Table I) ($R_1=$ $R_2=CH_3$, $R_3=H$, X is a carbon atom) was introduced into 4 ml of methanol, followed by addition, under argon and at room temperature, of finely ground potassium carbonate.

The solution quickly turned an orange color. It was left for 25 minutes and then filtered on a column of silica (eluent: pentane/ethyl ether). 0.037 g of a product corresponding to the expected structure, the polyene system of which was only partially reconjugated, was recovered. The yield was 54%.

EXAMPLE 21

Use of a compound of formula (I) to prepare retinal 0.125 g (0.439 mmol) of the compound obtained in Example 1 (Table 1)(in which X is a carbon atom) was dissolved in 2 ml of acetone. After cooling to 0° C., 0.35 ml of hydrobromic acid solution in acetone (c=0.127) was added. After one hour, the mixture was treated with NaHCO₃. It was diluted with Et₂O and washed with water. Chromatography on silica gave 0.072 g of retinal (57%).

EXAMPLE 22

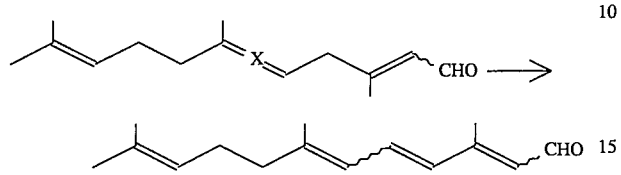

The same experimental procedure as in Example 21 was repeated, using the product obtained in Example 8 wherein X is a carbon atom. The product obtained was dehydrofarnesal, which was obtained with a yield of 75%.

EXAMPLE 23

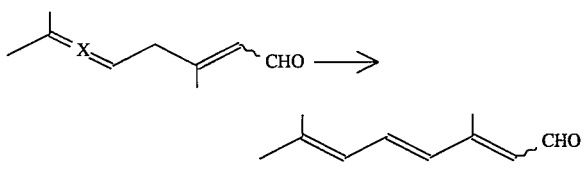

The same experimental procedure as in Example 20 was repeated, using the product obtained in Example 2 wherein X is a carbon atom. The product obtained was dehydrocitral, which was obtained with a yield of 54%.

TABLE 1

| | PREPARATION OF THE CARBONATE | | | | REARRANGEMENT | | | |
| --- | --- | --- | --- | --- | --- | --- | --- | --- |
| EXAMPLES | $R_1$ | $R_2$ | $R_3$ | Carbonate yield | Rearrangement catalyst | Yield Ia + Ib | Ia % | Ib % |
| 1 | [cyclohexene structure] | $CH_3$ | H | 78% | $Pd(PPh_3)_4$ | 54 | 86 | 14 |
| 2 | $CH_3$ | $CH_3$ | H | 64.5% | $Pd(PPh_3)_4$ | 59 | 36 | 64 |
| 3 | H | H | H | 51% | $Pd(PPh_3)_4$ | 64 | 0 | 100 |
| 4 | [cyclohexane structure] | | H | 31% | $Pd(PPh_3)_4$ | 69 | 100 | 0 |
| 5 | $CH_3$ | $CH_3$ | [isobutenyl] | 73% | $Pd(PPh_3)_4$ | 51 | 100 | 0 |
| 6 | $CH_3$ | $CH_3$ | [phenyl] | 90% | $Pd(PPh_3)_4$ | 89,5 | 100 | 0 |
| 7 | $CH_3$ | $CH_3$ | TMS | 81.5% | $Pd(PPh_3)_4$ | 30 | 63 | 37 |
| 8 | [isopentenyl] | $CH_3$ | H | 71% | $Pd(PPh_3)_4$ | 51 | 90 | 10 |
| 9 | [phenyl] | $CH_3$ | H | 78% | $Pd(PPh_3)_4$ | 35 | 66 | 33 |

TABLE 2

| EXAMPLES | Carbonate | Rearrangement catalyst | Ligand | Yield Ia + Ib | Ia | Ib |
| --- | --- | --- | --- | --- | --- | --- |
| 10 | ex 2 | Pd (DBA)₂ | Pd(PpH₃)₄ | 58 | 82 | 18 |

TABLE 2-continued
| EXAMPLES | Carbonate | Rearrangement catalyst | Ligand | Yield Ia + Ib | Ia | Ib |
|---|---|---|---|---|---|---|
| 11 | ex 2 | Pd (DBA)$_2$ | 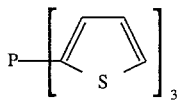 | 70 | 50 | 50 |
| 12 | ex 2 | Ni(PPh3)$_4$ | | 33 | 100 | 0 |
| 13 | ex 2 | Pd (DBA)$_2$ | 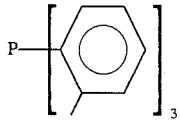 | 50 | 45 | 55 |

TABLE 3*
| EXAMPLES | PREPARATION OF THE CARBONATE | | REARRANGEMENT | |
|---|---|---|---|---|
| | $R^1$ | CARBONATE | YIELD Ia | Ib |
| 14 | 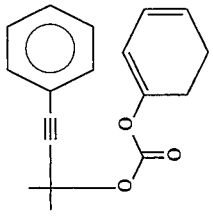 | 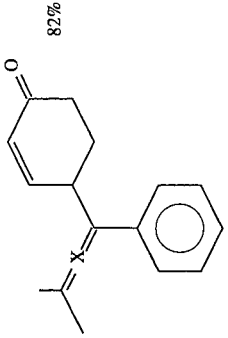 | 60.5 | 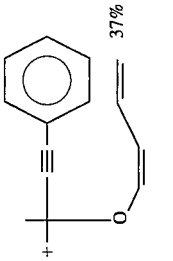 82% |
| 15 | 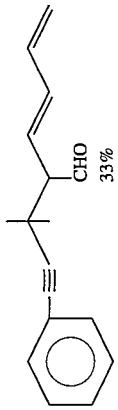 | 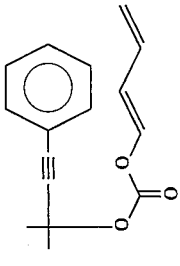 | 87 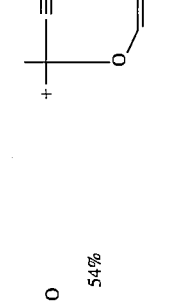 54% | 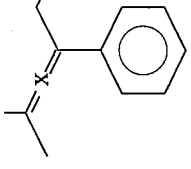 37% |
| 16 |  | 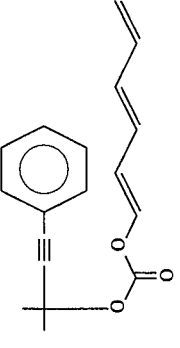 | 67 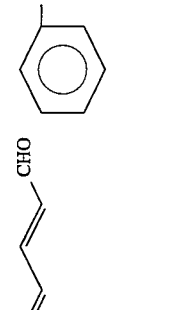 56% | 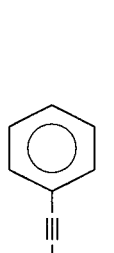 33% |
| 17 | 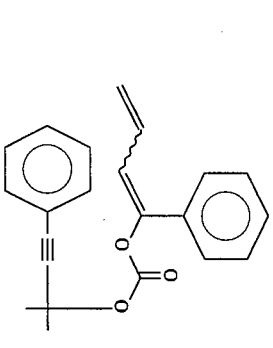 | 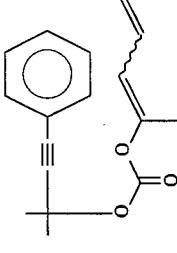 | 48 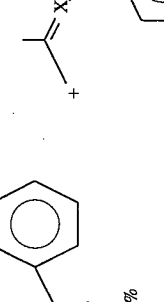 50% | 37% |

TABLE 3*-continued

| | PREPARATION OF THE CARBONATE | | REARRANGEMENT | |
|---|---|---|---|---|
| EXAMPLES | R¹ | CARBONATE | YIELD | Ia | Ib |
| 18 | (isopropenyl) | (2-phenylethynyl-prop-2-yl vinyl carbonate) | 86 | (rearranged product, 3.5%) | (phenyl propargyl cation, 66%) |

*wherein X is a carbon atom.

What is claimed:

1. A process for the preparation of an intermediate of formula (I)

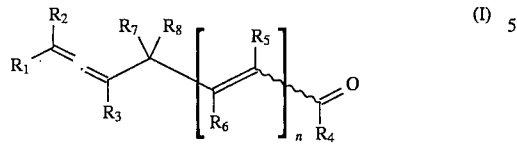

in which:

n is equal to 1 or 2, $R_1$, $R_2$ and $R_3$, each independently represent hydrogen, alkyl containing 1 carbon atom, alkenyl containing 2 to 11 carbon atoms, aryl, cycloalkenyl, or $R_1$ and $R_2$ can, together with the carbon atom to which they are attached, form a cycloalkyl compound, $R_4$, $R_5$, $R_6$, $R_7$ and $R_8$, each independently represent hydrogen, alkyl containing 1 carbon atom, alkenyl containing 2 to 10 carbon atoms or aryl containing 6 carbon atoms, or any two of $R_4$, $R_5$, $R_6$, $R_7$ and $R_8$ may together form, along with the carbon atom(s) to which they are attached, a cycloalkylidene group containing 3 to 10 carbon atoms, wherein an intermediate of formula (II):

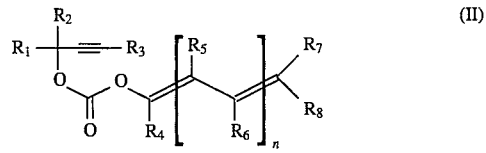

in which n, $R_1$, $R_2$, $R_3$, $R_4$, $R_5$, $R_6$, $R_7$ and $R_8$ are as defined above, is rearranged in an aprotic solvent in the presence of a catalyst selected from nickel and palladium and in the presence of a ligand which is a phosphine for a time sufficient to obtain a compound of formula (I).

2. A process according to claim 1, wherein the amount of catalyst used ranges from 1 to 20 mol % relative to the intermediate of formula (II).

* * * * *